United States Patent
Liu et al.

(10) Patent No.: US 10,696,702 B2
(45) Date of Patent: Jun. 30, 2020

(54) PROPYL-BRIDGED DIPHOSPHINE LIGANDS FOR ALKOXYCARBONYLATION

(71) Applicant: EVONIK DEGUSSA GMBH, Essen (DE)

(72) Inventors: Jiawang Liu, Henan (CN); Kaiwu Dong, Bo Zhou (CN); Robert Franke, Marl (DE); Helfried Neumann, Rostock (DE); Ralf Jackstell, Rostock (DE); Matthias Beller, Ostseebad Nienhagen (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 16/269,940

(22) Filed: Feb. 7, 2019

(65) Prior Publication Data

US 2019/0248817 A1    Aug. 15, 2019

(30) Foreign Application Priority Data

Feb. 14, 2018 (EP) .................................. 18156675

(51) Int. Cl.
*C07F 9/58* (2006.01)
*C07F 15/00* (2006.01)
*C07C 67/38* (2006.01)

(52) U.S. Cl.
CPC ................ *C07F 9/58* (2013.01); *C07C 67/38* (2013.01); *C07F 15/0066* (2013.01)

(58) Field of Classification Search
None
See application file for complete search history.

(56) References Cited

U.S. PATENT DOCUMENTS

| 5,175,244 A | 12/1992 | Budzelaar et al. |
| 8,106,186 B2 * | 1/2012 | Kodama ................. C07F 1/005 540/145 |
| 9,688,604 B2 | 6/2017 | Jennerjahn et al. |
| 9,725,398 B2 | 8/2017 | Dong et al. |
| 10,077,228 B2 | 9/2018 | Dong et al. |
| 2017/0022137 A1 | 1/2017 | Dong et al. |
| 2017/0022138 A1 | 1/2017 | Dong et al. |
| 2017/0022139 A1 | 1/2017 | Dong et al. |
| 2017/0022234 A1 | 1/2017 | Jennerjahn et al. |
| 2017/0022235 A1 | 1/2017 | Dong et al. |
| 2017/0022236 A1 | 1/2017 | Dong et al. |

FOREIGN PATENT DOCUMENTS

EP    3 121 180 A2    1/2017

OTHER PUBLICATIONS

Kapdi et al, Chemical Society Reviews, Manuscript ID: CS-REV-02-2014-000063.R1, pp. 1-31, submitted Mar. 23, (Year: 2014).*
European Search Report dated Jun. 26, 2018 in EP 18156675.3 (5 pages).
Singapore Search Report dated Dec. 11, 2019 for Singapore Patent Application No. 10201901187X (2 pages).

* cited by examiner

*Primary Examiner* — Zinna Northington Davis
(74) *Attorney, Agent, or Firm* — Smith, Gambrell & Russell, LLP.

(57) ABSTRACT

Propyl-bridged diphosphine compounds, metal complexes of these compounds and the use thereof for alkoxycarbonylation.

24 Claims, No Drawings

PROPYL-BRIDGED DIPHOSPHINE LIGANDS FOR ALKOXYCARBONYLATION

The invention relates to propyl-bridged diphosphine compounds, to metal complexes of these compounds and to the use thereof for alkoxycarbonylation.

The alkoxycarbonylation of ethylenically unsaturated compounds is a process of increasing significance. An alkoxycarbonylation is understood to mean the reaction of ethylenically unsaturated compounds (olefins) with carbon monoxide and alcohols in the presence of a metal-ligand complex to give the corresponding esters. Typically, the metal used is palladium. The following scheme shows the general reaction equation of an alkoxycarbonylation:

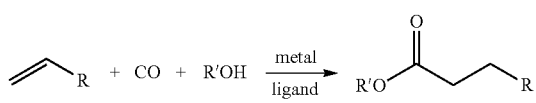

EP 3 121 180 A2 describes a process for alkoxycarbonylation and the ligands used for this purpose. In this process, butyl-bridged diphosphine compounds are used.

The problem addressed by the present invention is that of providing novel ligands for alkoxycarbonylation, with which good yields of esters can be achieved.

This problem is solved by compounds according to Claim 1.

Compound of the formula (1)

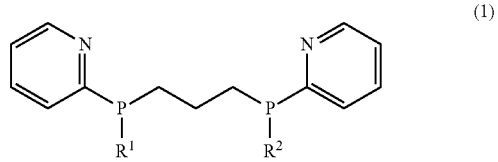

wherein $R^1$ and $R^2$ are each independently $-(C_1-C_{12})$-alkyl.

In one embodiment, $R^1$ and $R^2$ are the same radical.
In one embodiment, $R^1$ is $^tBu$.
In one embodiment, $R^2$ is $^tBu$.
In one embodiment, the compound has the structure (L1):

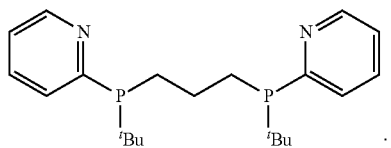

In addition to the compounds described above, a complex is also claimed which comprises one of the compounds described above and Pd.

Complex comprising Pd and a compound described above.

In addition to the complex and the compound, a process is also claimed in which these are used.

Process comprising the process steps of:
a) initially charging an ethylenically unsaturated compound;
b) adding a compound described above and a compound comprising Pd, or adding a complex described above;
c) adding an alcohol;
d) feeding in CO;
e) heating the reaction mixture, with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of CO is fed in.

In one variant of the process, the ethylenically unsaturated compound is selected from: ethene, propene, 1-butene, cis-2-butene, trans-2-butene, isobutene, 1,3-butadiene, 1-pentene, cis-2-pentene, trans-2-pentene, 2-methyl-1-butene, 3-methyl-1-butene, 2-methyl-2-butene, hexene, tetramethylethylene (2,3-dimethyl-2-butene), heptene, 1-octene, 2-octene, di-n-butene, or mixtures thereof.

In one variant of the process, the ethylenically unsaturated compound is tetramethylethylene.

In one variant of the process, the compound in process step b), comprising Pd, is selected from:
$PdCl_2$, $PdBr_2$, $Pd(acac)_2$, $Pd(dba)_2$ (dba=dibenzylideneacetone), $PdCl_2(CH_3CN)_2$.

In one variant of the process, the compound in process step b), comprising Pd, is $Pd(acac)_2$.

In one variant of the process, the alcohol in process step c) is selected from: methanol, ethanol, 1-propanol, 1-butanol, 1-pentanol, 1-hexanol, 2-propanol, tert-butanol, 3-pentanol, cyclohexanol, phenol, or mixtures thereof.

In one variant of the process, the alcohol in process step c) is methanol.

In one variant of the process, the reaction mixture is heated in process step e) to a temperature in the range from 80° C. to 160° C.

In one variant of the process, the reaction mixture is heated in process step e) to a temperature in the range from 100° C. to 140° C.

In one variant of the process, CO is fed in in process step d) such that the reaction proceeds at a CO pressure in the range from 20 bar to 50 bar.

In one variant of the process, CO is fed in in process step d) such that the reaction proceeds at a CO pressure in the range from 30 bar to 50 bar.

In one variant of the process, the process comprises the additional process step f):
f) adding p-toluenesulfonic acid.

The invention is more particularly elucidated hereinbelow with reference to working examples.

GENERAL PROCEDURE SPECIFICATIONS

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative procedures were effected in baked-out vessels. The products were characterized by means of NMR spectroscopy, Chemical shifts (δ) are reported in ppm. The $^{31}P$ NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E, Hoffman and Kurt W. Zilm, Pure Appl. Chem., 2008, 80, 59-84).

Nuclear resonance spectra were recorded on Bruker Avance 300 or Bruker Avance 400, gas chromatography analysis on Agilent GC 7890A, ESI-TOF mass spectrometry on Thermo Electron Finnigan MAT 95-XP and Agilent 6890 N/5973 instruments.

Preparation of chloro-2-pyridyl-tert-butylphosphine (Precursor A)

The Grignard for the synthesis of chloro-2-pyridyl-t-butylphosphine is prepared by the "Knochel method" with isopropylmagnesium chloride (Angew. Chem. 2004, 43, 2222-2226). The workup is effected according to the method of Budzelaar (Organometallics 1990, 9, 1222-1227).

Scheme 1: Synthesis of precursor A

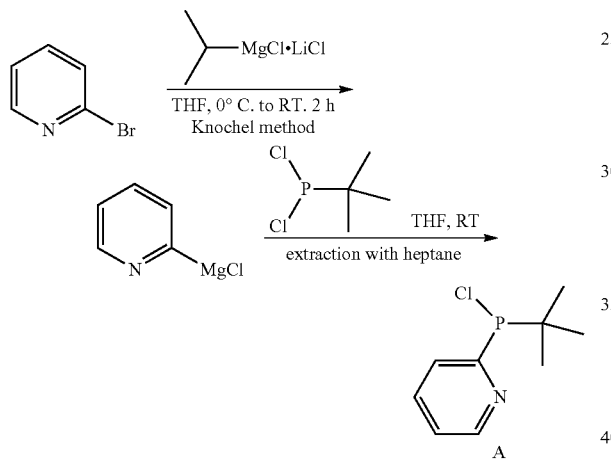

8.07 ml of a 1.3 M isopropylmagnesium chloride solution (Knochel's reagent) are introduced under argon into a 50 ml round-bottom flask with magnetic stirrer and septum, and cooled to −15° C. Thereafter, 954 μl (10 mmol) of 2-bromopyridine are rapidly added dropwise. The solution immediately turns yellow. It is allowed to warm up to −10° C. The conversion of the reaction is determined as follows: about 100 μl of solution are taken and introduced into 1 ml of a saturated ammonium chloride solution. If the solution "bubbles", not much Grignard has formed yet. The aqueous solution is extracted with a pipette of ether and the organic phase is dried over $Na_2SO_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion. Now the Grignard solution is slowly added dropwise with a syringe pump to a solution of 1.748 g (11 mmol) of dichloro-tert-butylphosphine in 10 ml of THF which has been cooled to −15° C. beforehand. The dichloro-tert-butylphosphine solution is cooled. A clear yellow solution is initially formed, which then turns cloudy. The mixture is left to warm up to room temperature and to stir overnight. The solvent is removed under high vacuum and a whitish solid which is brown in places is obtained. The solid is suspended with 20 ml of heptane and the solid is comminuted in an ultrasound bath. After allowing the white solid to settle, the solution is decanted. The operation is repeated twice with 10-20 ml each time of heptane. After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data:

$^1$H NMR (300 MHz, $C_6D_6$): δ 8.36; (m, 1H, py), 7.67; (m, 1H, py), 7.03-6.93; (m, 1H, py), 6.55-6.46; (m, 1H, py), 1.07; (d, J=13.3 Hz, 9H, t-Bu).

$^{13}$C NMR (75 MHz, $C_6D_6$): δ 162.9, 162.6, 148.8, 135.5, 125.8, 125.7, 122.8, 35.3, 34.8, 25.9 and 25.8.

$^{31}$P NMR (121 MHz, $C_6D_6$) δ 97.9.

MS (EI) m:z (relative intensity) 201 (M$^+$, 2), 147 (32), 145 (100), 109 (17), 78 (8), 57.1 (17).

Preparation of Compound (L1)

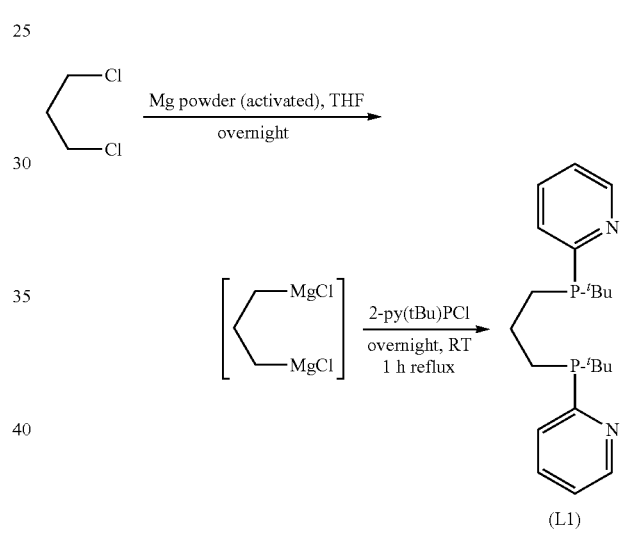

(Analogous to Graham Eastham et al., U.S. Pat. No. 6,335,471)

Comparative Ligands

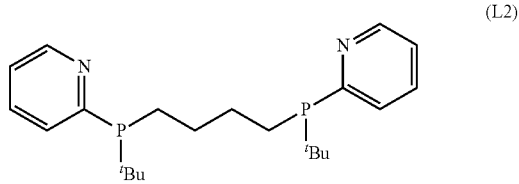

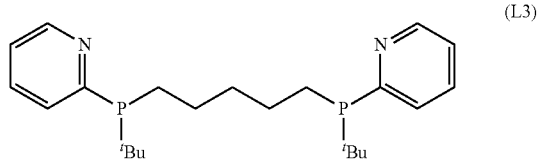

-continued

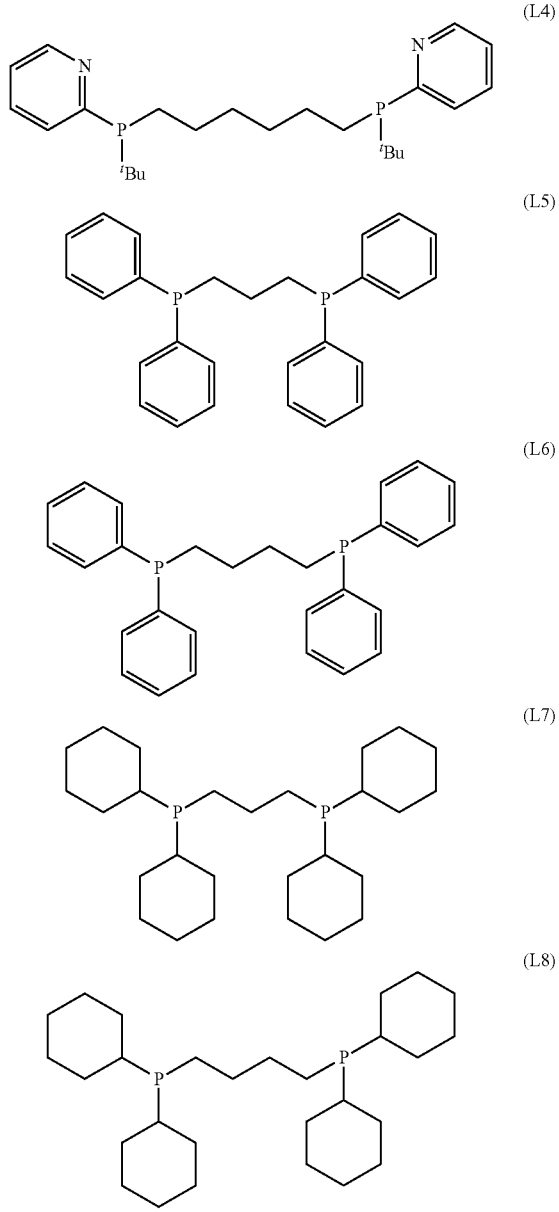

Methoxycarbonylation of Tetramethylethylene (1a)

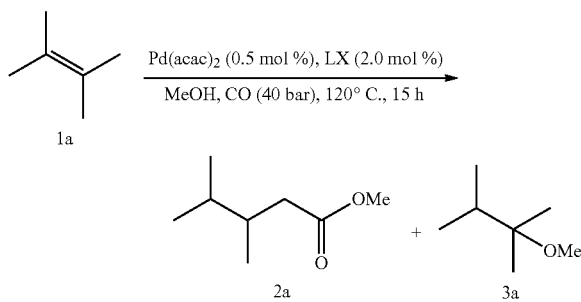

General Experimental Method for Autoclave Experiments in Glass Vials

A 300 ml Parr reactor is used. Matched to this is an aluminium block of corresponding dimensions which has been manufactured in-house and which is suitable for heating by means of a commercially available magnetic stirrer, for example from Heidolph. For the inside of the autoclave, a round metal plate of thickness about 1.5 cm was manufactured, containing 6 holes corresponding to the external diameter of the glass vials. Matching these glass vials, they are equipped with small magnetic stirrers. These glass vials are provided with screw caps and suitable septa and charged, using a special apparatus manufactured by glass blowers, under argon with the appropriate reactants, solvents and catalysts and additives. For this purpose, 6 vessels are filled at the same time; this enables the performance of 6 reactions at the same temperature and the same pressure in one experiment. Then these glass vessels are closed with screw caps and septa, and a small syringe cannula of suitable size is used to puncture each of the septa. This enables gas exchange later in the reaction. These vials are then placed in the metal plate and the latter is transferred into the autoclave under argon. The autoclave is purged with CO and filled at room temperature with the CO pressure intended. Then, under magnetic stirring by means of the magnetic stirrer, the autoclave is heated to reaction temperature and the reaction is conducted for the appropriate period. Subsequently, the autoclave is cooled down to room temperature and the pressure is slowly released. Subsequently, the autoclave is purged with nitrogen. The vials are taken from the autoclave, and a defined amount of a suitable standard is added. A GC analysis is effected, the results of which are used to determine yields and selectivities.

Methoxycarbonylation

A 4 ml vial was charged with tetramethylethylene (1a) (1.0 mol), and a magnetic stirrer bar was added. Thereafter there were added: $Pd(acac)_2$ (1.52 mg, 0.5 mol %), L1 (2.0 mol %), PTSA*$H_2O$ (16.0 mg, 8.0 mol %), MeOH (2.0 ml). The vial was placed onto a sample holder which was in turn inserted into a 300 ml Parr autoclave under an argon atmosphere. After the autoclave had been purged three times with nitrogen, the $CO$ pressure was adjusted to 40 bar. The reaction proceeded at 120° C. for 15 hours. On conclusion of the reaction, the autoclave was cooled down to room temperature and cautiously decompressed. Yield and regioselectivity were determined by means of GC.

The experiment described above was repeated with the comparative ligands (L2) to (L8). All other parameters were maintained. The results of the experimental series are compiled in the following table:

TABLE

| Ligand (LX) | Conversion [%] | Yield 2a [%] | Yield 3a [%] |
|---|---|---|---|
| L1* | >99 | 99 | 0 |
| L2 | 92 | 84 | 7 |
| L3 | 49 | 4 | 41 |
| L4 | 52 | 2 | 44 |
| L5 | 48 | 2 | 43 |
| L6 | 63 | 22 | 31 |
| L7 | 54 | 0 | 45 |
| L8 | 48 | 0 | 45 |

*inventive compound

As is shown by the results shown above, the problem is solved by the compound according to the invention.

The invention claimed is:

1. A metal-ligand complex comprising Pd and a compound of the formula (1)

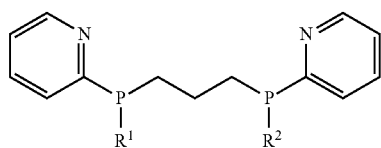

(1)

wherein $R^1$ is $^tBu$ and $R^2$ is -($C_1$-$C_{12}$)-alkyl.

2. The complex according to claim 1, wherein it has the structure (L1):

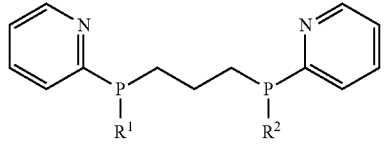

(L1)

3. A process for preparing an ester comprising:
a) initially charging an ethylenically unsaturated olefin, thereby forming a reaction mixture;
b) adding a compound having the formula:

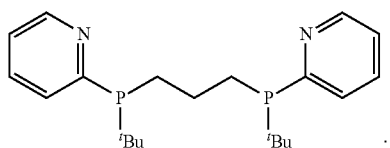

wherein $R^1$ and $R^2$ are each independently -($C_1$-$C_{12}$)-alkyl,
and a compound comprising Pd;
c) adding an alcohol;
d) feeding in CO;
e) heating the reaction mixture, thereby converting the CO, alcohol and ethylenically unsaturated compound to form the ester.

4. The process according to claim 3, wherein the ethylenically unsaturated compound is selected from:
ethene, propene, 1-butene, cis-2-butene, trans-2-butene, isobutene, 1,3-butadiene, 1-pentene, cis-2-pentene, trans-2-pentene, 2-methyl-1-butene, 3-methyl-1-butene, 2-methyl-2-butene, hexene, tetramethylethylene (2,3-dimethyl-2-butene), heptene, 1-octene, 2-octene, di-n-butene or mixtures thereof.

5. The process according to claim 3, wherein the compound in process step b), comprising Pd, is selected from:
$PdCl_2$, $PdBr_2$, $Pd(acac)_2$, $Pd(dba)_2$ (dba=dibenzylideneacetone) or $PdCl_2(CH_3CN)_2$.

6. The process according to claim 3, wherein the alcohol in process step c) is selected from:
methanol, ethanol, 1-propanol, 1-butanol, 1-pentanol, 1-hexanol, 2-propanol, tert-butanol, 3-pentanol, cyclohexanol, phenol or mixtures thereof.

7. The process according to claim 3, wherein the reaction mixture is heated in process step e) to a temperature in the range from 80° C. to 160° C.

8. The process according to claim 3, wherein CO is fed in in process step d) such that the reaction proceeds at a CO pressure in the range from 20 bar to 50 bar.

9. The process according to claim 3, wherein the process comprises the additional process step f):
f) adding p-toluenesulfonic acid.

10. The process according to claim 3, where $R^1$ and $R^2$ are the same radical.

11. The process according to claim 3, where $R^1$ is $^tBu$.

12. The process according to claim 3, where $R^2$ is $^tBu$.

13. The process according to claim 3, wherein the compound has the structure (L1):

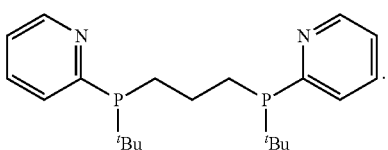

(L1)

14. A process for preparing an ester comprising:
a) initially charging an ethylenically unsaturated olefin, thereby forming a reaction mixture;
b) adding a complex according to claim 1;
c) adding an alcohol;
d) feeding in CO;
e) heating the reaction mixture, with conversion of the ethylenically unsaturated compound to an ester.

15. The process according to claim 14, wherein the ethylenically unsaturated compound is selected from:
ethene, propene, 1-butene, cis-2-butene, trans-2-butene, isobutene, 1,3-butadiene, 1-pentene, cis-2-pentene, trans-2-pentene, 2-methyl-1-butene, 3-methyl-1-butene, 2-methyl-2-butene, hexene, tetramethylethylene (2,3-dimethyl-2-butene), heptene, 1-octene, 2-octene, di-n-butene or mixtures thereof.

16. The process according to claim 14, wherein the Pd in process step b), is sourced from:
$PdCl_2$, $PdBr_2$, $Pd(acac)_2$, $Pd(dba)_2$ (dba=dibenzylideneacetone) or $PdCl_2(CH_3CN)_2$.

17. The process according to claim 14, wherein the alcohol in process step c) is selected from;
methanol, ethanol, 1-propanol, 1-butanol, 1-pentanol, 1-hexanol, 2-propanol, tert-butanol, 3-pentanol, cyclohexanol, phenol or mixtures thereof.

18. The process according to claim 14, wherein the reaction mixture is heated in process step e) to a temperature in the range from 80° C. to 160° C.

19. The process according to claim 14, wherein CO is fed in in process step d) such that the reaction proceeds at a CO pressure in the range from 20 bar to 50 bar.

20. The process according to claim 14, wherein the process comprises the additional process step f):
f) adding p-toluenesulfonic acid.

21. The process according to claim 14, where $R^1$ and $R^2$ are the same radical.
22. The process according to claim 14, where $R^1$ is $^tBu$.
23. The process according to claim 14, where $R^2$ is $^tBu$.
24. The process according to claim 14, wherein the compound has the structure (L1):
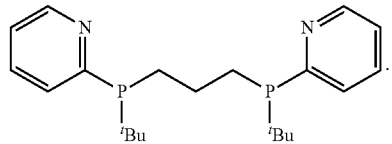
(L1)
\* \* \* \* \*